United States Patent [19]

Li

[11] Patent Number: 5,707,395

[45] Date of Patent: Jan. 13, 1998

[54] SURGICAL FASTENER AND METHOD AND APPARATUS FOR LIGAMENT REPAIR

[75] Inventor: Lehmann K. Li, Milford, Conn.

[73] Assignee: Li Medical Technologies, Inc., Shelton, Conn.

[21] Appl. No.: 784,234

[22] Filed: Jan. 16, 1997

[51] Int. Cl.⁶ .................................................. A61B 17/04
[52] U.S. Cl. ............................................................ 606/232
[58] Field of Search ............................................. 606/232

[56] References Cited

U.S. PATENT DOCUMENTS

| | | |
|---|---|---|
| 34,293 | 6/1862 | Goble et al. . |
| 34,762 | 10/1862 | Goble et al. . |
| 1,247,621 | 11/1917 | Bennett . |

(List continued on next page.)

FOREIGN PATENT DOCUMENTS

| | | |
|---|---|---|
| 0270704 | 6/1988 | European Pat. Off. . |
| 1368021 | 6/1964 | France . |
| 2622430 | 5/1989 | France . |
| 343992 | 3/1931 | United Kingdom . |
| 9204874 | 4/1992 | WIPO . |

OTHER PUBLICATIONS

Acufex Microsurgical, Inc., "Single Incision Fixation . . . EndoButton™ As Easy as Passing the Graft".

Mitek Surgical Products, Inc., "The Mitek Ligament Anchor System".

Y. Ishibashi et al., "The Effect Of The ACL Graft Fixation Level On Knee Stability", Musculoskeletal Research Center, Department of Orthopaedic Surgery, University of Pittsburgh Medical Center, pp. 151–156.

Marc J. Friedman, MD, "Patellar Tendon Versus Hamstring ACL Reconstruction", Southern California Orthopedic Institute, Feb. 25, 1996, pp. 182–188.

Linvatec, "The BioScrew Fixation System", 1995.

John Cherf, MD, MPH et al., "Graft Fixation For Anterior Cruciate Ligament Reconstruction" Orthopedic Special Edition, Jun. 1996, pp. 48–51.

Instrument Makar, Inc. "PerFixation™ ACL System", Jun. 1994, pp. 1–12.

(List continued on next page.)

*Primary Examiner*—Gary Jackson
*Attorney, Agent, or Firm*—Ostrolenk, Faber, Gerb & Soffen, LLP

[57] ABSTRACT

Apparatus and method for anchoring a ligament or ligament replacement into a bone comprising an expandable member for insertion into a borehole formed in the bone, the expandable member having an exterior gripping surface for engaging with the borehole and a central longitudinally extending channel, the expandable member connecting to the ligament or ligament replacement, an expanding member for disposition in the channel of the expandable member for movement in the channel to expand the expandable member in the borehole; the expanding member having a passageway therein aligned with the channel, a cable slidably traversing the passageway and the channel and extending proximally from the expanding member for gripping by an installation tool, a stop member disposed on the cable for engaging a distal surface of the expandable member for preventing further proximal slidable movement of the cable in the passageway and channel, the expanding member having a proximal surface for engagement by the installation tool, the cable grasped by the installation tool with the stop member abutting the expandable member and the installation tool abutting the proximal surface of the expanding member, the installation tool applying a force to the cable to move the expanding member relatively with respect to the expandable member to expand the expandable member so that the gripping surface of the expandable member grips the sidewall of the borehole to secure the expandable member in the borehole and secure the ligament or ligament replacement to the bone.

57 Claims, 7 Drawing Sheets

U.S. PATENT DOCUMENTS

| | | |
|---|---|---|
| 2,100,570 | 11/1937 | Saleh . |
| 2,143,086 | 1/1939 | Pleister . |
| 2,213,715 | 9/1940 | Monahan . |
| 2,453,056 | 11/1948 | Zack . |
| 2,562,419 | 7/1951 | Ferris . |
| 3,048,177 | 8/1962 | Takaro . |
| 3,143,915 | 8/1964 | Tendler . |
| 3,155,095 | 11/1964 | Brown . |
| 3,227,031 | 1/1966 | Williams . |
| 3,254,650 | 6/1966 | Collito . |
| 3,316,796 | 5/1967 | Young . |
| 4,011,602 | 3/1977 | Rybicki et al. . |
| 4,233,981 | 11/1980 | Schomacher . |
| 4,293,259 | 10/1981 | Liebig . |
| 4,379,451 | 4/1983 | Getscher . |
| 4,447,915 | 5/1984 | Weber . |
| 4,454,612 | 6/1984 | McDaniel et al. . |
| 4,501,266 | 2/1985 | McDaniel . |
| 4,525,114 | 6/1985 | Hirst . |
| 4,632,100 | 12/1986 | Somers et al. . |
| 4,636,121 | 1/1987 | Miller . |
| 4,708,132 | 11/1987 | Silvestrini . |
| 4,738,255 | 4/1988 | Goble et al. . |
| 4,741,330 | 5/1988 | Hayhurst . |
| 4,744,793 | 5/1988 | Parr et al. . |
| 4,747,407 | 5/1988 | Liu et al. . |
| 4,759,765 | 7/1988 | Van Kampen . |
| 4,772,286 | 9/1988 | Goble et al. . |
| 4,776,330 | 10/1988 | Chapman et al. . |
| 4,828,562 | 5/1989 | Kenna . |
| 4,870,957 | 10/1989 | Goble et al. . |
| 4,875,474 | 10/1989 | Border . |
| 4,892,547 | 1/1990 | Brown . |
| 4,898,156 | 2/1990 | Gatturna . |
| 4,899,743 | 2/1990 | Nicholson et al. . |
| 4,901,711 | 2/1990 | Goble et al. . |
| 4,911,153 | 3/1990 | Border . |
| 4,927,421 | 5/1990 | Goble et al. . |
| 4,946,468 | 8/1990 | Li . |
| 4,950,270 | 8/1990 | Bowman et al. . |
| 4,959,071 | 9/1990 | Brown et al. . |
| 4,960,420 | 10/1990 | Goble et al. . |
| 4,968,315 | 11/1990 | Gatturna . |
| 4,985,032 | 1/1991 | Goble . |
| 4,986,263 | 1/1991 | Dickerson et al. . |
| 4,997,433 | 3/1991 | Goble et al. . |
| 5,002,550 | 3/1991 | Li . |
| 5,002,574 | 3/1991 | May et al. . |
| 5,011,473 | 4/1991 | Gatturna . |
| 5,013,316 | 5/1991 | Goble et al. . |
| 5,019,105 | 5/1991 | Wiley . |
| 5,037,422 | 8/1991 | Hayhurst et al. . |
| 5,037,426 | 8/1991 | Goble et al. . |
| 5,046,513 | 9/1991 | Gatturna . |
| 5,062,843 | 11/1991 | Mahony, III . |
| 5,078,730 | 1/1992 | Li ............................ 606/232 |
| 5,084,058 | 1/1992 | Li ............................ 606/232 |
| 5,087,263 | 2/1992 | Li . |
| 5,092,891 | 3/1992 | Kummer et al. . |
| 5,094,563 | 3/1992 | Carletti . |
| 5,129,902 | 7/1992 | Goble et al. ............ 606/232 |
| 5,133,723 | 7/1992 | Li et al. . |
| 5,141,520 | 8/1992 | Goble et al. ............ 606/232 |
| 5,147,166 | 9/1992 | Harker . |
| 5,147,362 | 9/1992 | Goble ..................... 606/232 |
| 5,152,764 | 10/1992 | Goble ..................... 606/232 |
| 5,152,790 | 10/1992 | Rosenberg et al. . |
| 5,161,916 | 11/1992 | White et al. . |
| 5,163,946 | 11/1992 | Li . |
| 5,174,087 | 12/1992 | Bruno . |
| 5,176,682 | 1/1993 | Chow . |
| 5,192,303 | 3/1993 | Gatturna et al. . |
| 5,203,787 | 4/1993 | Noblitt et al. ........... 606/232 |
| 5,207,679 | 5/1993 | Li ............................ 606/232 |
| 5,211,647 | 5/1993 | Schmieding . |
| 5,217,486 | 6/1993 | Rice et al. . |
| 5,224,946 | 7/1993 | Hayhurst et al. . |
| 5,236,445 | 8/1993 | Hayhurst et al. . |
| 5,250,058 | 10/1993 | Miller et al. . |
| 5,263,802 | 11/1993 | Fichot et al. . |
| 5,263,991 | 11/1993 | Wiley et al. . |
| 5,266,075 | 11/1993 | Clark et al. . |
| 5,268,001 | 12/1993 | Nicholson et al. . |
| 5,282,802 | 2/1994 | Mahony, III . |
| 5,300,077 | 4/1994 | Howell . |
| 5,306,290 | 4/1994 | Martins et al. . |
| 5,312,416 | 5/1994 | Spaeth et al. . |
| 5,312,422 | 5/1994 | Trott . |
| 5,312,438 | 5/1994 | Johnson . |
| 5,313,962 | 5/1994 | Obenchain . |
| 5,314,427 | 5/1994 | Goble et al. . |
| 5,314,429 | 5/1994 | Goble . |
| 5,314,433 | 5/1994 | Li . |
| 5,318,577 | 6/1994 | Li . |
| 5,324,308 | 6/1994 | Pierce . |
| 5,330,534 | 7/1994 | Herrington et al. . |
| 5,342,366 | 8/1994 | Whiteside et al. . |
| 5,350,380 | 9/1994 | Goble et al. . |
| 5,354,298 | 10/1994 | Lee et al. . |
| 5,354,300 | 10/1994 | Goble et al. . |
| 5,356,413 | 10/1994 | Martins et al. . |
| 5,358,511 | 10/1994 | Gatturna et al. . |
| 5,366,457 | 11/1994 | McGuire et al. . |
| 5,372,599 | 12/1994 | Martins . |
| 5,372,604 | 12/1994 | Trott . |
| 5,376,120 | 12/1994 | Sarver et al. . |
| 5,383,878 | 1/1995 | Roger et al. . |
| 5,393,302 | 2/1995 | Clark et al. . |
| 5,397,357 | 3/1995 | Schmieding et al. . |
| 5,411,522 | 5/1995 | Trott . |
| 5,417,691 | 5/1995 | Hayhurst . |
| 5,425,733 | 6/1995 | Schmieding . |
| 5,443,482 | 8/1995 | Stone et al. . |
| 5,443,509 | 8/1995 | Boucher et al. . |
| 5,454,811 | 10/1995 | Huebner . |
| 5,458,601 | 10/1995 | Young, Jr. et al. . |
| 5,464,425 | 11/1995 | Skiba . |
| 5,464,427 | 11/1995 | Curtis et al. . |
| 5,480,403 | 1/1996 | Lee et al. . |
| 5,486,197 | 1/1996 | Le et al. . |
| 5,489,210 | 2/1996 | Hanosh . |
| 5,500,001 | 3/1996 | Trott . |
| 5,531,792 | 7/1996 | Huene . |
| 5,534,004 | 7/1996 | Santangelo . |
| 5,545,180 | 8/1996 | Le et al. . |
| 5,562,668 | 10/1996 | Johnson . |
| 5,562,669 | 10/1996 | McGuire . |

OTHER PUBLICATIONS

Akira Maeda, MD, et al., "Anterior Cruciate Ligament Reconstruction with Multistranded Autogenous Semitendinosus Tendon", The American Journal of Sports Medicine, vol. 24, No. 4, pp. 504–509.

F. Alan Barber et al., "The Ultimate Strength of Suture Anchors", Arthroscopy: The Journal of Arthroscopic and Related Surgery, vol. 11, No. 1, Feb., 1195, pp. 21–28.

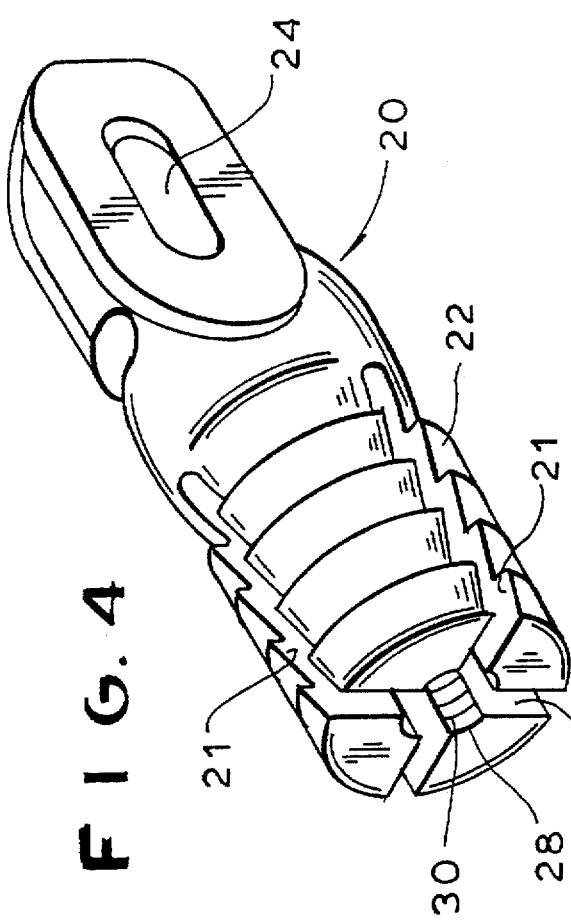
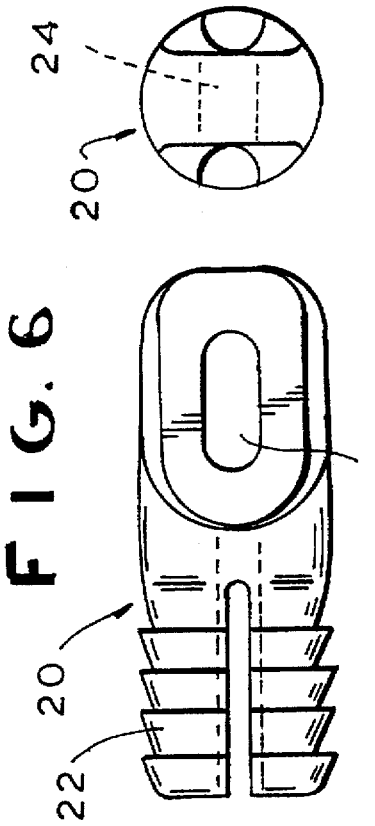
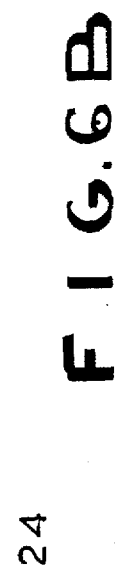
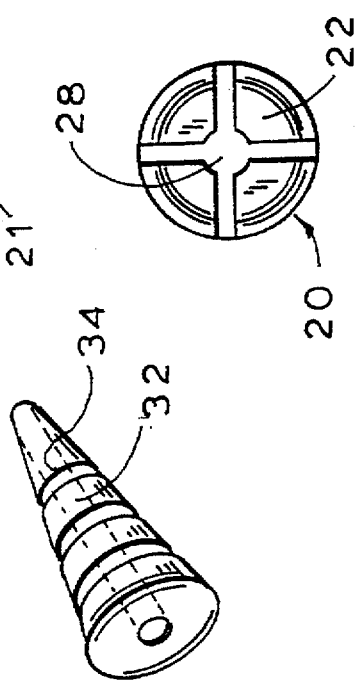

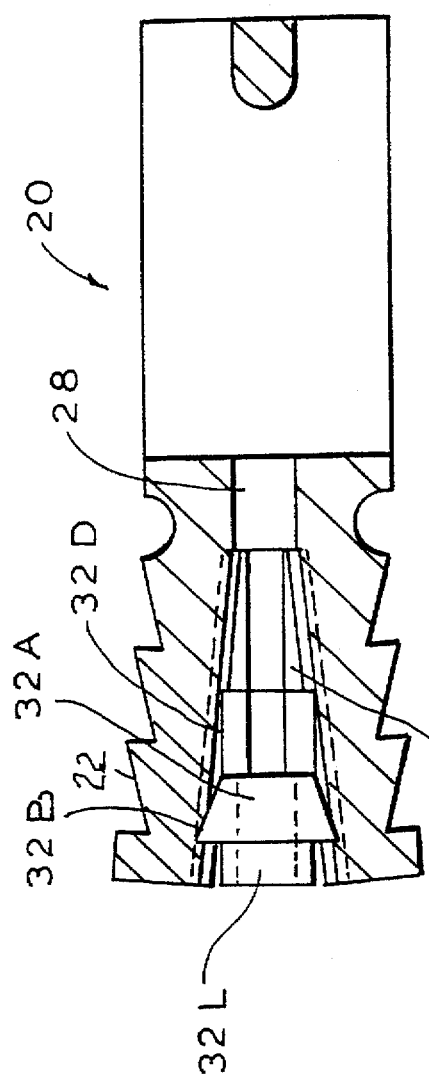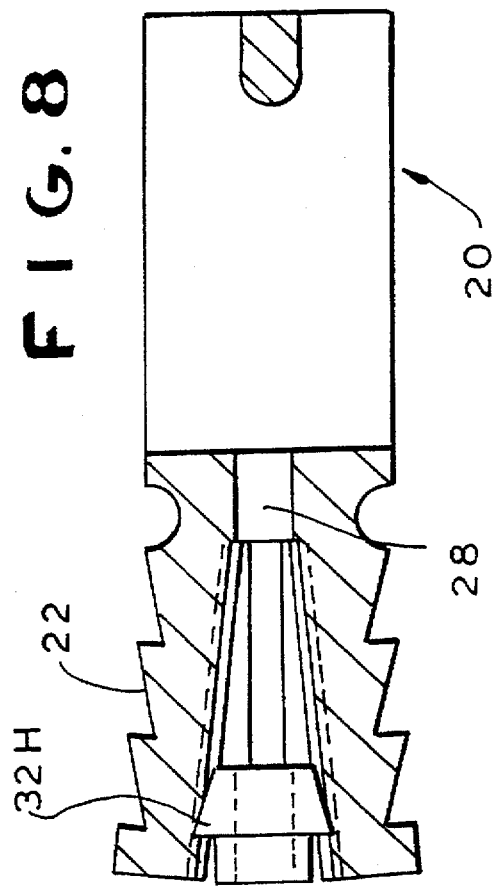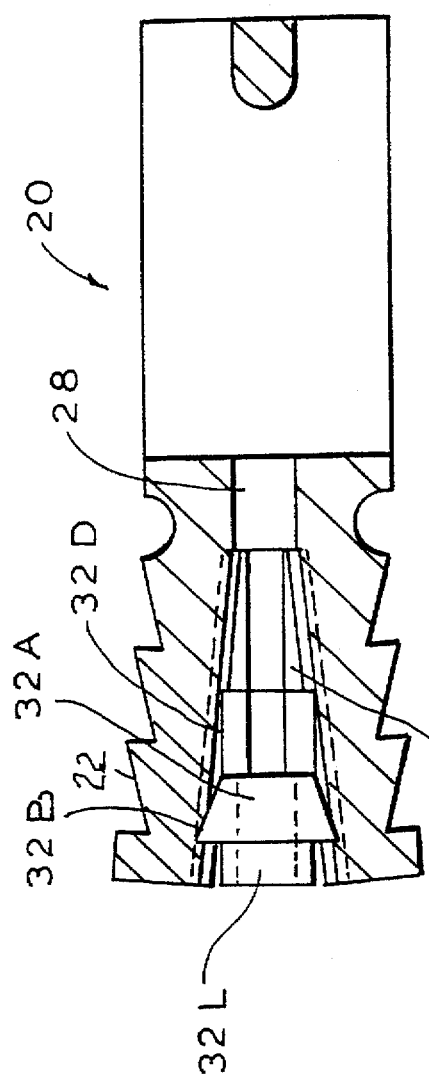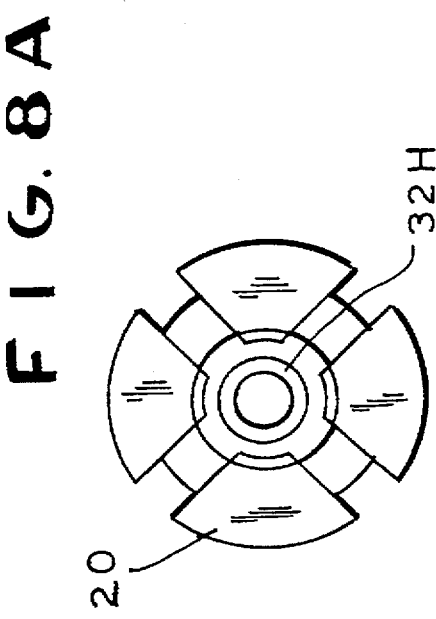

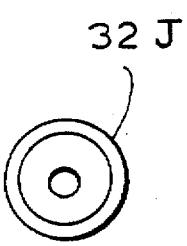 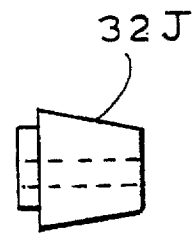
FIG. 9A    FIG. 9
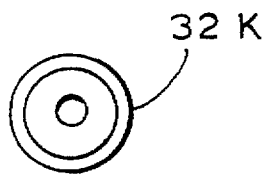 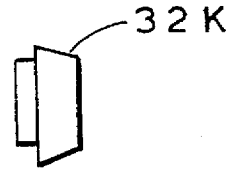
FIG. 10A    FIG. 10
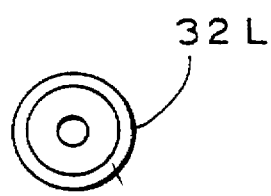 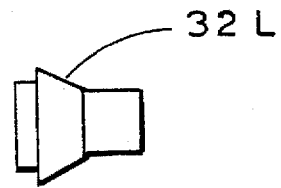
FIG. 11A    FIG. 11
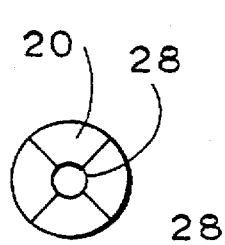 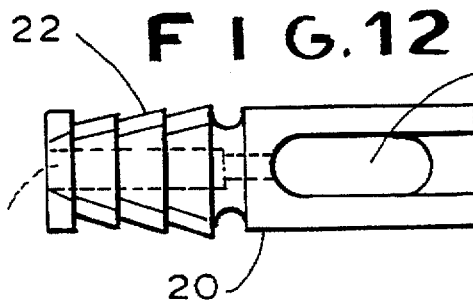 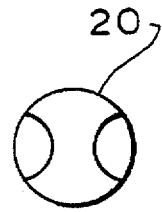
FIG. 12B    FIG. 12A

SURGICAL FASTENER AND METHOD AND APPARATUS FOR LIGAMENT REPAIR

BACKGROUND OF THE INVENTION

The present invention relates to surgical fasteners, e.g., anchors for fastening sutures or prosthesis to organic tissue, e.g. bone. It also relates to the repair of ligaments in human or animal bodies, and in particular, to the repair of ligaments in bodily joints using natural or prosthetic ligament replacements. With respect to the latter aspect, the present invention relates to a ligament repair apparatus and method employing surgical anchors for securing the ligament replacement in the respective bones of a bodily joint. An example of the application of the invention is to the repair or replacement of the cruciate ligaments, for example, the anterior cruciate ligament of the human knee.

Various anchor devices are known for implantation in organic tissue, such as bone. The known devices are used for fastening sutures to bone or for providing a post for the fixation of a prosthesis. Some of the known devices screw into the bone. Others utilize an expansion effect to provide securement into a borehole. See e.g., U.S. Pat. No. 5,480,403. Still others use the action of radially extending fingers to anchor the fastener in the organic medium. See applicant's copending application Ser. No. 08/294,067, filed Aug. 22, 1994 entitled Anchor and Method for Securement into a bore.

Some known anchors have a frangible connection so that a portion of the anchor breaks away to be disposed of, leaving the anchoring portion in the organic medium. Also, some of the prior art devices are made of biocompatible metals, which can be difficult to remove if placed improperly.

Various devices and methods are also known for the repair of ligaments, and in particular, the anterior cruciate ligament of the human knee. The applicant of this application has a co-pending patent application Ser. No. 08/465,559 entitled Method and Apparatus for Securing Ligaments, which is directed to the repair of and replacement of ligaments, and in particular, this co-pending application shows methods and apparatus for cruciate ligament repair.

Various other methods and apparatus for ligament repair are known.

Some of the known techniques suffer from various disadvantages including the bulky nature of the equipment necessary to set the anchors which secure the ligament in the bone sections of the bodily joint. Additionally, most of the known devices utilize biocompatible metallic fastening elements which, although effective, can be problematical in the event that the initial securement is defective, for example, the tension in the ligament is improper due to imprecise location of the anchor in the bore hole drilled in the bone of the joint. In such situations, it may be necessary to remove the previously replaced anchor. This cannot be done by simple drilling techniques with metallic anchors. Furthermore, many of the techniques require screw-type systems which set the anchor into the bone or interference screws to secure the anchor or a bone block into the bone. These are problematical because they require the exertion of potentially tissue damaging rotational forces.

SUMMARY OF THE INVENTION

It is, accordingly, an objection of the present invention to provide a surgical fastening device for anchoring into an organic medium, e.g. bone.

It is yet still a further object of the invention to provide a suture or prosthesis anchor.

It is a further object of the present invention to provide a method and apparatus for ligament repair and/or replacement.

Yet still a further object of the present invention is to provide such a method and apparatus for ligament repair and/or replacement which is easy and convenient to implement.

It is yet still a further object of the present invention to provide a method and apparatus for ligament replacement and/or repair which does not require the application of rotational forces.

Yet still a further object of the present invention is to provide a method and apparatus for ligament repair and/or replacement which uses a quick acting axially generated force to set the anchors into the bones of the joint.

Yet still a further object of the present invention is to provide a method and apparatus for ligament repair and/or replacement which utilizes anchors which can be easily removed, for example by drilling, once they have been secured into the bone, in the event that a different positioning is found to be necessary.

Yet another object of the invention is to provide a method and apparatus for ligament replacement and/or repair which allows easy setting of the required tension in the ligament or ligament replacement.

The above and other objects of the present invention are achieved by an apparatus for anchoring a ligament or ligament replacement into a bone comprising a first expandable member for insertion into a borehole formed in the bone, the expandable member having an exterior gripping surface for engaging with a sidewall of the borehole and a central longitudinally extending channel, the expandable member having a connecting location for connecting to a ligament or ligament replacement, a first expanding member for disposition in a proximal end of the channel of the expandable member for longitudinal movement in the channel to expand the expandable member in the borehole; the expanding member having a longitudinally extending passageway therein aligned with the channel in the expandable member, a longitudinally extending member slidably traversing the passageway in the expanding member and the channel in the expandable member and extending proximally from the expanding member for gripping by an installation tool, a stop member disposed on the longitudinally extending member for engaging a surface of the expandable member at a distal end of the channel for preventing further proximal slidable movement of the longitudinally extending member in the passageway and channel, the expanding member having a proximal surface for engagement by the installation tool, the longitudinally extending member being adapted to be grasped by the installation tool with the stop member abutting the surface of the expandable member at the distal end of the channel and the installation tool abutting the proximal surface of the expanding member, the longitudinally extending member being adapted to have a force applied thereto by the installation tool thereby to move the expanding member relatively with respect to the expandable member in the channel to expand the expandable member so that the gripping surface of the expandable member grips the sidewall of the borehole to secure the expandable member in the borehole and thereby secure the ligament or ligament replacement to the bone.

The above and other objects of the invention are also achieved by an apparatus for anchoring a ligament or ligament replacement between opposed bones of a bodily joint, comprising a first expandable member for insertion into a first borehole formed in a first bone of the joint, the expandable member having an exterior gripping surface for engaging with a sidewall of the first borehole and a central longitudinally extending channel, the expandable member having a connecting location for connecting to a first end of the ligament or ligament replacement, a first expanding member for disposition in a proximal end of the channel of the first expandable member for longitudinal movement in the channel to expand the first expandable member in the first borehole; the first expanding member having a longitudinally extending passageway therein aligned with the channel in the first expandable member, a longitudinally extending member slidably traversing the passageway in the first expanding member and the channel in the first expandable member and extending proximally from the first expanding member for gripping by an installation tool, a first stop member disposed on the longitudinally extending member for engaging a surface of the first expandable member at a distal end of the channel for preventing further proximal slidable movement of the longitudinally extending member in the passageway and channel, the first expanding member having a proximal surface for engagement by the installation tool, the longitudinally extending member being adapted to be grasped by the installation tool with the first stop member abutting the surface of the first expandable member at the distal end of the channel and the installation tool abutting the proximal surface of the first expanding member, the longitudinally extending member being adapted to have a force applied thereto by the installation tool thereby to move the first expanding member relatively with respect to the first expandable member in the channel to expand the first expandable member so that the gripping surface of the first expandable member grips the sidewall of the first borehole to secure the first expandable member in the first borehole and thereby secure the ligament or ligament replacement in the first bone; and further comprising, a second expandable member for insertion into a second borehole formed in a second bone of the joint opposed to the first bone, the second expandable member having an exterior gripping surface for engaging with a sidewall of the second borehole and a central longitudinally extending channel, the second expandable member having a connecting location for connecting to a second end of the ligament or ligament replacement, a second expanding member for disposition in a proximal end of the channel of the second expandable member for longitudinal movement in the channel to expand the second expandable member in the second borehole; the second expanding member having a longitudinally extending passageway therein aligned with the channel in the second expandable member, the longitudinally extending member slidably traversing the passageway in the second expanding member and the channel in the second expandable member and extending proximally from the second expanding member for gripping by the installation tool, a second stop member for engaging a surface of the second expandable member at a distal end of the channel for preventing further proximal slidable movement of the longitudinally extending member in the second passageway and second channel, the second expanding member having a proximal surface for engagement by the installation tool, the longitudinally extending member being adapted to be grasped by the installation tool with the second stop member abutting the surface of the second expandable member at the distal end of the channel and the installation tool abutting the proximal surface of the second expanding member, the longitudinally extending member being adapted to have a force applied thereto by the installation tool thereby to move the second expanding member relatively with respect to the second expandable member to expand the second expandable member so that the gripping surface of the second expandable member grips the sidewall of the second borehole to secure the second expandable member in the second borehole and thereby secure the ligament or ligament replacement to the second bone.

The above and other objects of the invention are furthermore achieved by a method for anchoring a ligament or ligament replacement into a bone comprising the steps of, forming a first borehole in the bone, providing a first expandable member for insertion into the first borehole formed in the bone, the first expandable member having an exterior gripping surface for engaging with a sidewall of the first borehole and a central longitudinally extending channel, connecting a ligament or ligament replacement to the first expandable member at a connecting location, providing a first expanding member for disposition in a proximal end of the channel of the first expandable member for longitudinal movement in the channel to expand the first expandable member in the first borehole; the first expanding member having a longitudinally extending passageway therein aligned with the channel in the first expandable member, disposing a longitudinally extending member slidably traversing the passageway in the expanding member and the channel in the first expandable member and extending proximally from the expanding member for gripping by an installation tool, providing a stop member on the longitudinally extending member for engaging a surface of the first expandable member at a distal end of the channel for preventing further proximal slidable movement of the longitudinally extending member in the passageway and channel, the first expanding member having a proximal surface for engagement by the installation tool, inserting the first expandable member, first expanding member and the longitudinally extending member in the first borehole so that the channel in the expandable member is in alignment with the passageway in the expanding member and the longitudinally extending member traverses the passageway and channel; grasping the longitudinally extending member with the installation tool with the stop member abutting the surface of the first expandable member at the distal end of the channel and abutting the proximal surface of the first expanding member with the installation tool; and applying an axial force to the longitudinally extending member with the installation tool thereby to move the first expanding member relatively with respect to the first expandable member to expand the first expandable member so that the gripping surface of the first expandable member grips the sidewall of the borehole to secure the first expandable member in the first borehole and thereby secure the ligament or ligament replacement to the bone.

The objects of the invention are also achieved by a surgical fastener for securement into a borehole in an organic medium, comprising, a first expandable member for insertion into the borehole formed in the organic medium, the expandable member having an exterior gripping surface for engaging with a sidewall of the borehole and a central longitudinally extending channel, a first expanding member for disposition in a proximal end of the channel of the expandable member for longitudinal movement in the channel to expand the expandable member in the borehole, the expanding member having a longitudinally extending passageway aligned with the channel in the expandable member, a longitudinally extending member traversing the passageway in the expanding member and the channel in the expandable member and extending proximally from the expanding member for gripping by an installation tool, a stop member disposed on the longitudinally extending member for engaging a surface of the expandable member at a distal end of the channel for preventing further proximal slidable movement of the longitudinally extending member in the channel, the expanding member having a proximal surface for engagement by the installation tool, the longitudinally extending member being adapted to be grasped by the installation tool with the stop member abutting the surface of the expandable member at the distal end of the channel and the installation tool abutting the proximal surface of the expanding member, the longitudinally extending member being adapted to have a force applied thereto by the installation tool thereby to move the expanding member relatively with respect to the expandable member in the channel to expand the expandable member so that the gripping surface of the expandable member grips the side wall of the borehole to secure the expandable member in the borehole.

Other objects, features and advantages of the invention will be apparent from the detailed description which follows.

BRIEF DESCRIPTION OF THE DRAWINGS

The above and other objects of the present invention will be apparent from the detailed description which follows, taken in conjunction with the following drawings in which:

FIG. 3 is a schematic view of a portion of an alternative embodiment of the present invention;

FIG. 4 is a perspective view of the expandable member of the ligament anchor according to the present invention;

FIG. 5 is a perspective view of an expanding member which is used in conjunction with the expandable member shown in FIG. 4;

FIG. 6 is a side plan view of the member shown in FIG. 4;

FIG. 6A is an end view of the member shown in FIG. 4;

FIG. 6B is a second end view of the member shown in FIG. 4;

FIG. 7 is a cross-sectional side plan view of another embodiment of an expandable member and expanding member;

FIG. 7A is an end view of FIG. 7;

FIG. 8 is a cross-sectional side plan view of yet another expandable member and expanding member;

FIG. 8A is an end view of FIG. 8;

FIGS. 9 and 9A show respectively side and end views of another embodiment of the expanding member;

FIGS. 10 and 10A show respectively side and end views of another form of the expanding member;

FIG. 11 and 11A show side and end views, respectively, of yet still another embodiment of the expanding member;

FIG. 12 shows yet still another embodiment of an expandable member like that shown in FIG. 4;

FIGS. 12A and 12B show end views of the expandable member shown in FIG. 12;

DETAILED DESCRIPTION OF EMBODIMENTS OF THE INVENTION

Figure 1:
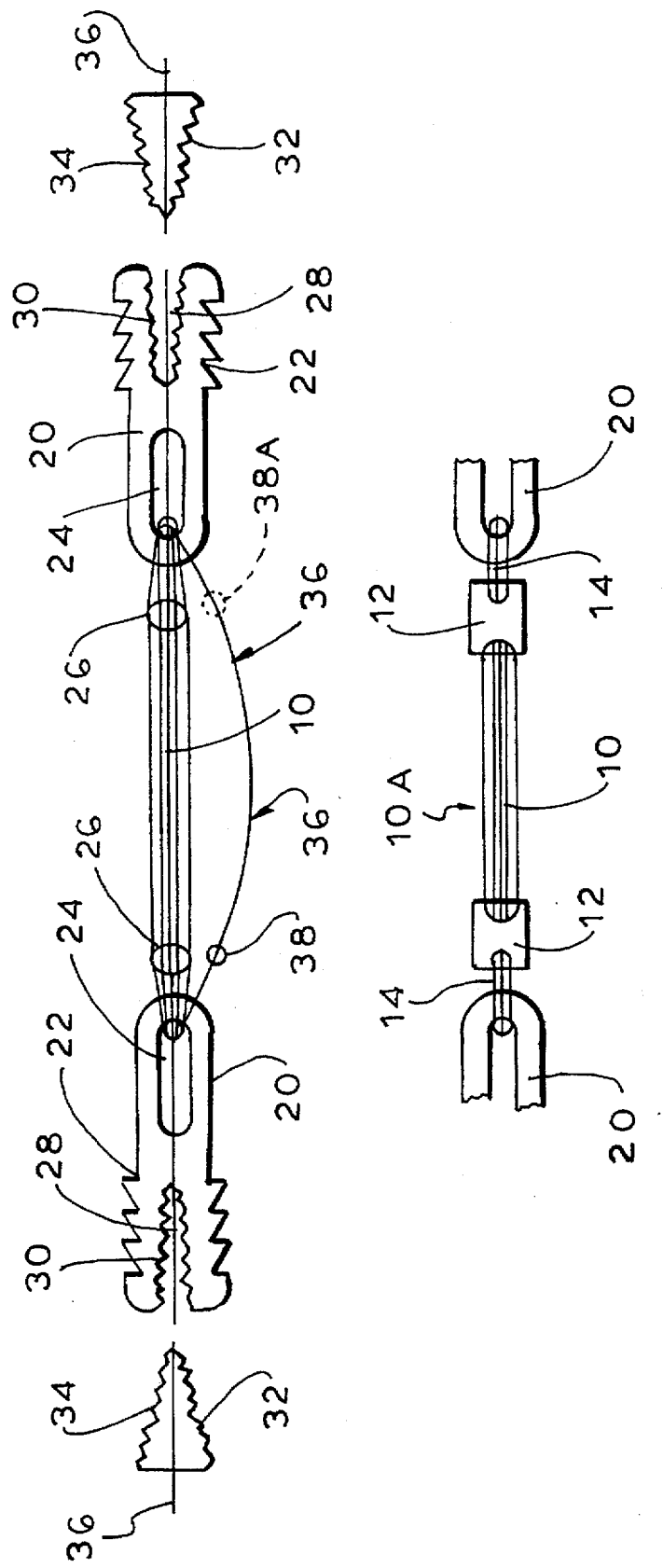
FIG. 1 is a schematic view of a ligament replacement and anchors according to the invention for securement to the respective bones of a bodily joint.

With reference now to the drawings, FIG. 1 shows in schematic view a ligament repair and/or replacement apparatus according to the present invention. The device is intended to be used with the existing torn ligament or a ligament replacement, for example, a prosthetic ligament or a natural ligament or tendon taken from another portion of the body, for example, the semitendinosus, or another suitable tendon or ligament. The ligament or ligament replacement 10 is attached, at each end, to an anchor body 20, each provided for securement into a borehole formed, for example, by drilling into opposed bones of the bodily joint. For example, the ligament to be repaired may be the anterior cruciate ligament of the human knee, and each of the members 20 may be secured into respective ones of the tibia and femur. This is shown schematically in FIG. 2 where T designates the tibia and F the femur.

The members 20 each comprise a longitudinally extending anchor member 20 having an outer engaging surface 22 which may comprise, for example, a plurality of serration, as shown. Preferably, the member 20 is made of a biocompatible plastic for ease of drilling out should the initial location of the device be imprecise. However, the member 20 can also be made of a suitable biocompatible metal.

The ligament or ligament replacement 10 is suitably secured to the anchor body 20, for example, by looping through an aperture 24 provided at distal end of member 20. The ligament or ligament replacement can be looped through the opening 24 and suitably secured, for example, by suturing 26.

Each body 20 includes a longitudinally extending channel 28 disposed therein. The longitudinally extending channel 28 preferably includes serrations or threads 30 disposed internally and may be tapered, as shown. The longitudinally extending channel 28 is adapted to receive an expanding member 32 which may comprise, for example, a conically shaped member which may have serrations or threads 34 disposed thereon for engagement with the internal serrations or threads 30 of the channel 28. Member 32 has a longitudinally extending aperture disposed therethrough, through which a member 36, which may be a cable wire or suture, is disposed. Member 36 extends through the member 32, through the member 20 and exits through the aperture 24 in the member 20 and then runs alongside the ligament replacement 10 and through the corresponding member 20 and 32 of the other anchor. Member 36 includes a crimped or welded ball or other stopping device 38, as shown. A second crimped ball or stopping device 38A may also be employed adjacent the other anchor, but it is not necessary. Alternatively, if member 36 is a suture, stopping device 38, 38A may comprise a suture knot.

Figure 2:
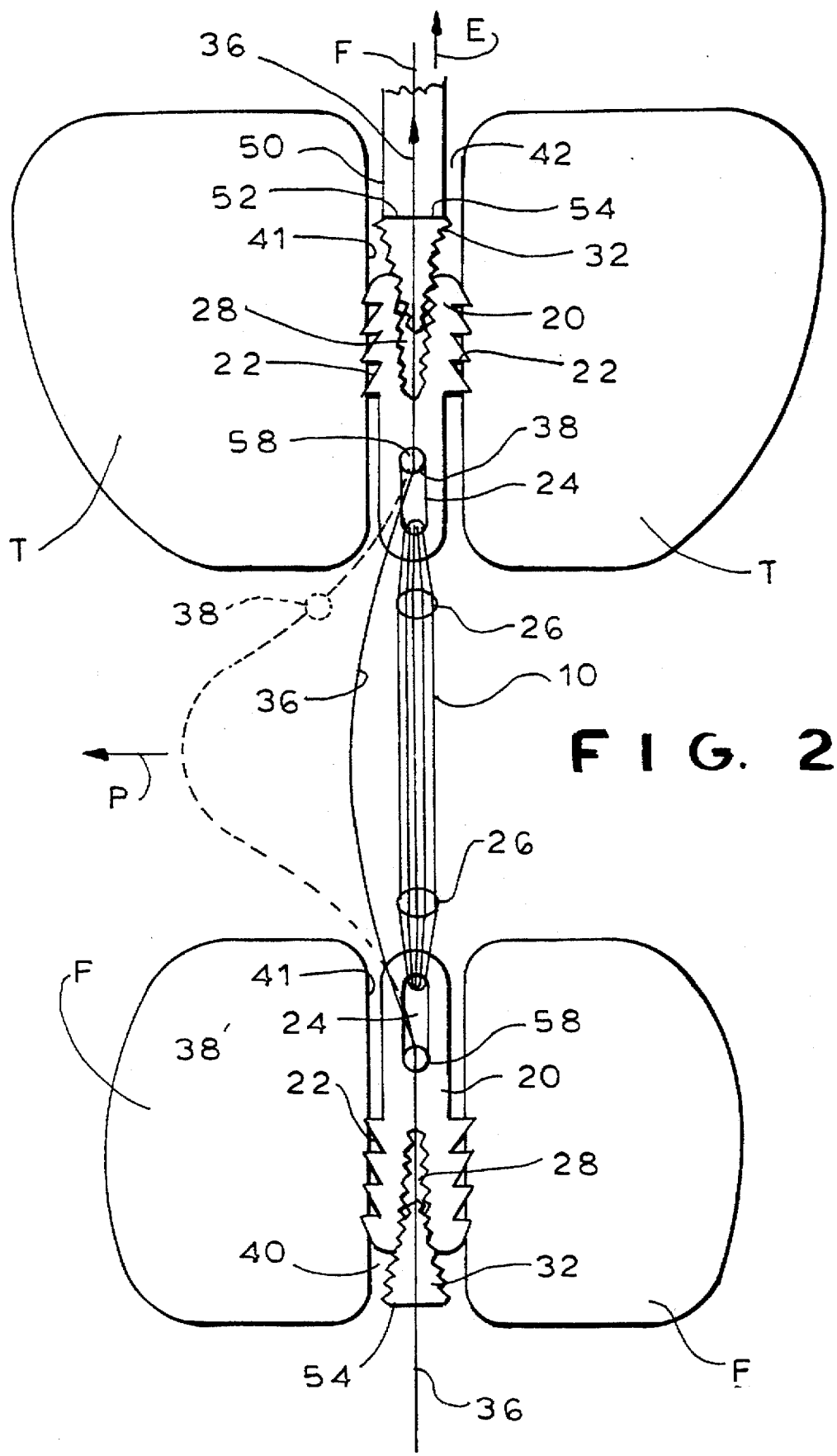
FIG. 2 is a schematic view of the method and apparatus of the invention.

FIG. 2 shows in a schematic view, the application of the device to the replacement of the anterior cruciate ligament. The tibia is indicated at T and the femur is shown at F, schematically.

FIG. 2 shows how the invention is employed. Boreholes 40 and 42 are respectively provided by known techniques in the opposed bones of the joint, for example, the femur and tibia bones. These openings are made in proper alignment for the location of the ligament or ligament replacement 10. The anchors 20 with the expanding members 32 positioned in or near the proximal ends of the channels 28 but not forcing the expandable members 20 into their expanded position, are coupled to the ligament or ligament replacement 10, which is provided by known surgical techniques. The ligament or ligament replacement 10 is suitably secured to each of the anchor members 20 by suturing or other known means. After the boreholes 40 and 42 are formed in the bones, the members 20 are inserted, preferably from between the joint, individually into the respective boreholes 40 and 42 and roughly located.

A first of the anchor members 20 is then secured into the respective borehole 40, 42 at the appropriate location using a tool 50, a portion of which is shown schematically in FIG. 2, and which has a surface 52 which engages with a proximal surface 54 of the expanding member 32.

The tool 50 includes a gripping means (not shown) for engaging the cable 36 and exerting a force in the direction of the arrow FE. Prior to engaging the member 36 with the tool 50, the crimped ball or stop member 38 is positioned in the opening 24 such that it abuts against proximal surface 58 of opening 24. After the member 36 is inserted into the tool 50 with the surface 52 engaging surface 54 of member 32, the tool 50 is actuated. The combination of the tool 50 bearing down on the surface 54 of member 32 and the upward pulling of force FE by the tool 50 causes the member 32 to move relatively longitudinally in the channel 28 with respect to member 20. Due to the relative movement of the member 32 in the expandable member 20, the outer gripping surfaces 22 of member 20 move outwardly and engage with the sidewall 41 of the borehole 40, 42. As shown in FIG. 4, the expandable member 20 can have a plurality of longitudinal slits 21 provided therein to allow the expansion to occur.

Once the member 20 has been secured in the one bone member, for example, the bone member T, a similar procedure is used to secure the other member 20 in the other bone member, for example the bone member F. Prior to attaching the tool 50 to the other end of member 36 to secure the still unsecured anchor member 20, the ball or stop member 38 is moved by sliding the member 36 longitudinally so that it is secured at the surface 58 of the other hole 24 in other member 20. This is shown by the circle drawn in phantom marked 38'. Alternatively, a second crimped ball or stop member 38A can be provided adjacent to other member 20, as shown in FIG. 1. Once the stop member 38, 38', 38A is in position, the tool T is again attached to the member 36. The appropriate tension is provided by pulling on the member 36 which will cause the appropriate tension to be provided to the ligament or ligament replacement 10. Once the appropriate tension has been provided, the tool is actuated to force the member 32 into the opening 28 to secure the member 20. After tool 50 is removed, member 36 is then removed from the joint by pulling from between the joint in the direction P, as shown by the dashed lines of FIG. 2. The process is then complete.

FIGS. 1 and 2 show the invention using a ligament or ligament replacement 10 which is sutured back on itself through the opening 24 to secure it to the member 20. Alternatively, if a bone-tendon-bone block is used, for example, a bone-tendon-bone block from the human knee, the bones 12 of the bone-tendon-bone block 10A may be secured to the anchor members 20 by suitable sutures 14 or any other suitable means. This is shown schematically in FIG. 3.

FIGS. 4, 5, 6, 6A and 6B show details of the members 20 and 32.

Although member 32 is shown as axially moving relatively into member 20 without rotation, the invention can be modified so that tool 50 rotates member 32 into member 20, with member 20 having internal threads 30 receiving external threads 34 on member 32. Member 32 accordingly screws into member 20, thereby causing the desired expansion of member 20 to secure the anchor.

FIG. 7 shows a cross-section through the member 20 in which a member 32A has been employed. This expanding member 32A includes a tapered portion 32B between two straight portions 32C and 32D. An additional tapered portion 32E is provided extending distally.

The expanding members 32, 32A can be made in various forms to achieve the desired expansion effect. FIG. 8 shows another embodiment 32H according to the present invention for expanding the member 32.

FIGS. 9, 9A, 10, 10A, 11 and 11A show various other forms of the expanding members 32. These are respectively indicated by 32J, 32K and 32L. The different members may be employed depending upon the hardness of the bone to which the anchor is being inserted. For example, it is known that the tibia bone is harder than the femur bone. Accordingly, the smaller, less lengthy member 32K may be employed to anchor in the tibia. Correspondingly, a larger expanding member 32J may be employed in the femur.

Figures 13, 14:
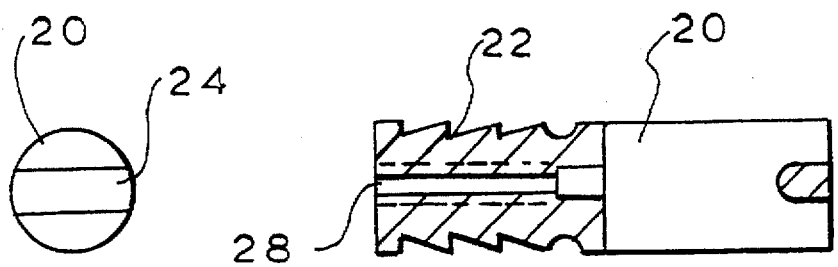
FIG. 13 shows the expandable member of FIG. 12 according to the view A—A of FIG. 12.
FIG. 14 shows the expandable member of FIG. 12 according to the view B—B of FIG. 12.

FIGS. 12, 12A, 12B, 13 and 14 show various views of another expandable member 20. FIGS. 12A and 12B show end views. FIG. 13 shows the view A—A of FIG. 12 and FIG. 14 shows the view B—B of FIG. 12.

Figure 15:
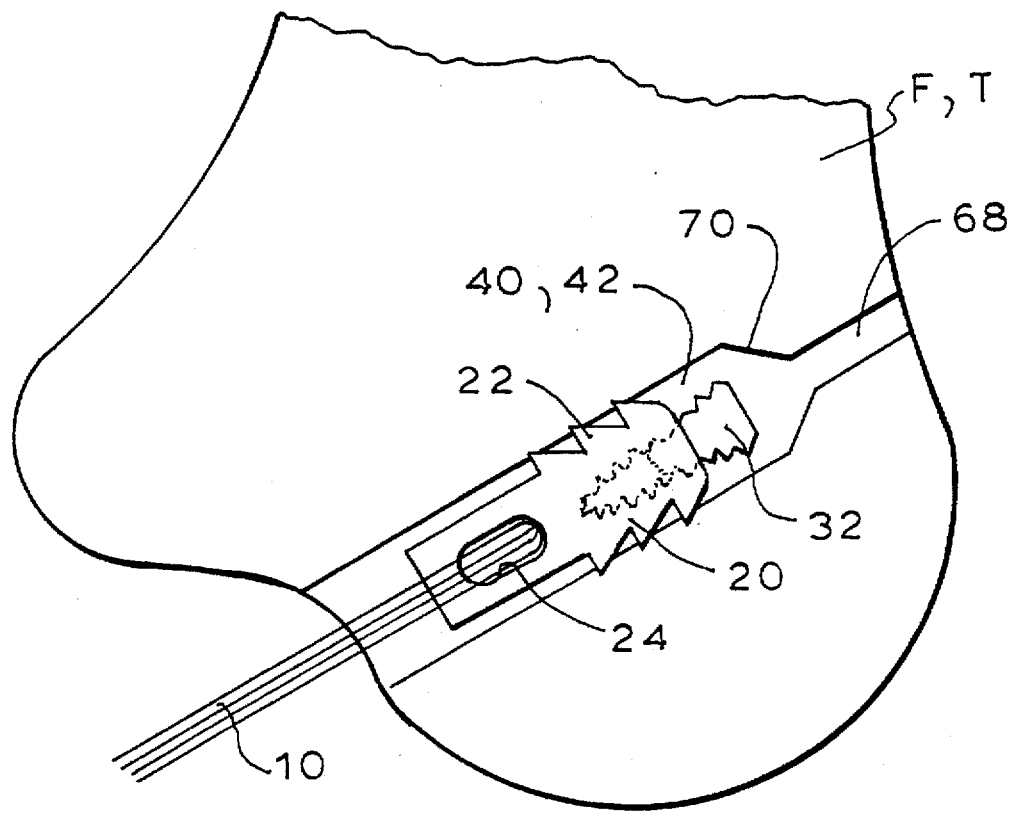
FIG. 15 shows a detail according to a further aspect of the present invention.

FIG. 15 shows that the invention can be employed by drilling a borehole 40, 42 in the affected bone, for example, the femur F or tibia T, without drilling the borehole of the required diameter to anchor the member 20 throughout the entire length of the borehole. In such case, the borehole may be drilled first with a smaller diameter drill bit completely through the bone F, T as indicated by the small diameter borehole 68. Thereafter, the borehole 40, 42 may be drilled, reamed or enlarged to the required diameter to a suitable depth 70 using a larger diameter drill or reamer, as shown.

Figure 16:
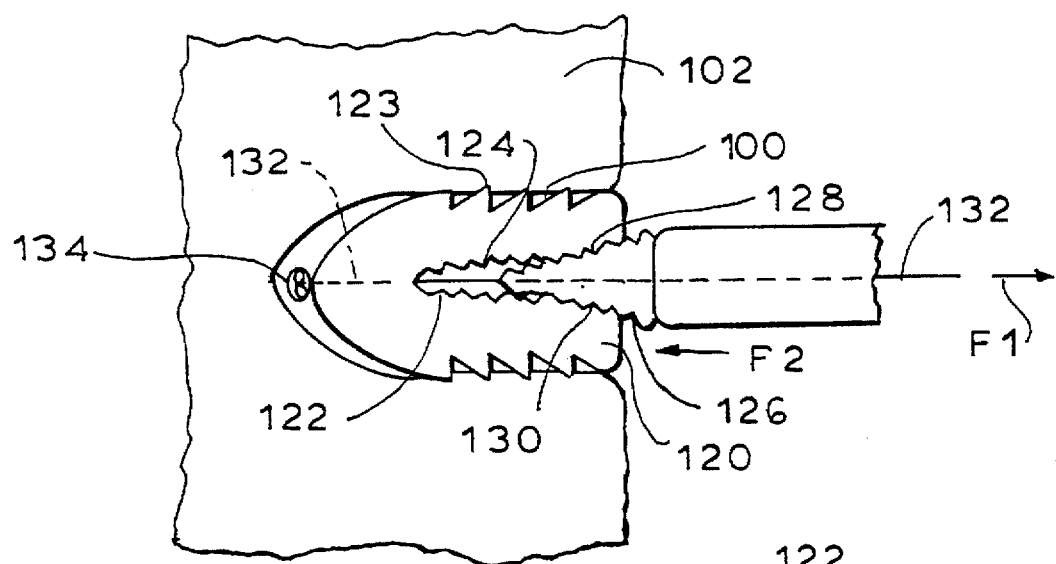
FIG. 16 shows a surgical anchoring device according to the present invention.

FIG. 16 shows a surgical fastener according to the present invention, and in particular, a suture anchor. An appropriate bore hole 100 is bored into the organic medium such as bone 102. The anchor comprises a first cylindrical expandable element 120 having a longitudinally extending channel 122 therein. The channel 122 has serrations, teeth or threads 124 at a proximal end. The expandable element 120 has suitable serrations or teeth 123 on its external surface to enable it to grip the sidewall of the borehole 100 when it is expanded. The channel 122 receives an expanding member 126 which has mating serrations, teeth or threads 128 externally and which engage with the internal serrations, teeth or threads 124 of the member 120. Member 126 includes a longitudinally extending channel 130 therein through which a suture 132 is received. Suture 132 extends through the channel 130 in member 126, through the channel 122 in the member 120 and terminates at a distal end of the member 120 in a knot 134.

In use, the suture 132 is threaded through the channels in members 126 and 120 and knotted at end 134. An installation tool 150, only a portion of which is shown, may be used to emplace the suture anchor comprising the members 120 and 126 in the bore hole 100 in the bone 102. Once the suture anchor is emplaced, a pulling force F1 is applied to the suture 132 while a pressing force F2 is applied by the installation tool 150 to the member 126. The combination of the pulling force F1 on the suture 132 and the pressing force F2 on the member 126 causes the member 126 to move relatively into the member 120, thereby expanding the member 120 into the bore hole 100.

Figure 17:
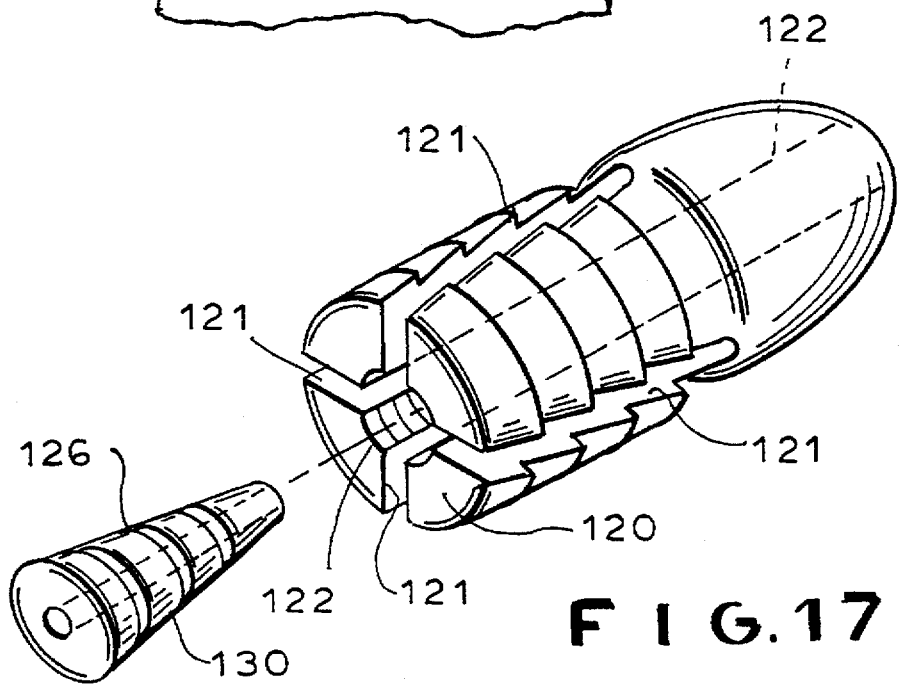
FIG. 17 is an exploded perspective view of the anchoring device of FIG. 16.

The member 120 is shown in perspective view in FIG. 17, and preferably includes a plurality of radially extending slots to allow the expansion to occur, as in the embodiment of FIG. 4.

The suture anchor shown in FIGS. 16 and 17 is preferably made of a biocompatible plastic. This allows it to be removed, for example by drilling, should it initially be emplaced improperly. In addition, the suture anchor of FIGS. 16 and 17 does not include any frangible connections, as in come prior art anchors, wherein a portion breaks away from the anchoring portion of the suture anchor. Also, the installation tool is relatively simple, not requiring any tapered cam surfaces to cause the securement of the anchor.

As in the other embodiments described, the expanding member 126 and expandable member 120 may have engaging threads so that member 126 can rotatingly thread into member 20 to cause the expansion of member 120.

Although the present invention has been described in relation to particular embodiments thereof, many other variations and modifications and other uses will become apparent to those skilled in the art. Therefore, the present invention should be limited not by the specific disclosure herein, but only by the appended claims.

What is claimed is:

1. Apparatus for anchoring a ligament or ligament replacement into a bone comprising:

a first expandable member for insertion into a borehole formed in the bone, the expandable member having an exterior gripping surface for engaging with a sidewall of the borehole and a central longitudinally extending channel;

the expandable member having a connecting location for connecting to a ligament or ligament replacement;

a first expanding member for disposition in a proximal end of the channel of the expandable member for longitudinal movement in the channel to expand the expandable member in the borehole; the expanding member having a longitudinally extending passageway therein aligned with the channel in the expandable member;

a longitudinally extending member slidably traversing the passageway in the expanding member and the channel in the expandable member and extending proximally from the expanding member for gripping by an installation tool;

a stop member disposed on the longitudinally extending member for engaging a surface of the expandable member at a distal end of the channel for preventing further proximal slidable movement of the longitudinally extending member in the passageway and channel;

the expanding member having a proximal surface for engagement by the installation tool;

the longitudinally extending member being adapted to be grasped by the installation tool with the stop member abutting the surface of the expandable member at the distal end of the channel and the installation tool abutting the proximal surface of the expanding member, the longitudinally extending member being adapted to have a force applied thereto by the installation tool thereby to move the expanding member relatively with respect to the expandable member in the channel to expand the expandable member so that the gripping surface of the expandable member grips the sidewall of the borehole to secure the expandable member in the borehole and thereby secure the ligament or ligament replacement to the bone.

2. The apparatus of claim 1, further comprising a second expandable member and second expanding member for disposition in an opposed bone of a bone joint for securing a second end of the ligament or ligament replacement to the opposed bone, the longitudinally extending member having a second end traversing through a passageway in the second expanding member and a channel of the second expandable member.

3. The apparatus of claim 2, wherein both expanding members and expandable members comprise a biocompatible plastic.

4. The apparatus of claim 2, wherein the longitudinally extending member is slidable in the two passageways and channels so that the stop member is movable from a location at a distal end of the first channel in the first expandable member to a location at a distal end of the channel in the second expandable member.

5. The apparatus of claim 2, further comprising a second stop member on the longitudinally extending member disposed for engagement with a surface adjacent a distal end of the second expandable member.

6. The apparatus of claim 2, wherein the first and second expanding members have different shapes dependent on the hardness of the bone into which the respective expandable member is inserted.

7. The apparatus of claim 1, wherein the expanding member comprises a conical member.

8. The apparatus of claim 1, wherein the expanding member has grooves or serration on an exterior surface for engaging with an interior surface of the channel.

9. The apparatus of claim 4, wherein the channel has serration or grooves for engaging with the expanding member.

10. The apparatus of claim 1, wherein the channel has serration or grooves for engaging with the expanding member.

11. The apparatus of claim 1, wherein the expanding member has threads on an exterior surface for engaging with threads on an interior surface of the channel.

12. The apparatus of claim 11, wherein the expanding member moves rotationally relatively into the expandable member.

13. The apparatus of claim 1, wherein the force comprises an axial force.

14. The apparatus of claim 1, wherein the expandable member has a longitudinal slot therein communicating with the channel to assist in expansion.

15. The apparatus of claim 10, wherein the expandable member has a plurality of longitudinal slots therein.

16. The apparatus of claim 1, wherein the connecting location on the expandable member comprises an opening for connection of the ligament or ligament replacement thereto.

17. The apparatus of claim 1, further comprising a ligament or ligament replacement coupled to the connecting location.

18. The apparatus of claim 17, wherein the ligament or ligament replacement comprises a natural ligament replacement.

19. The apparatus of claim 18, wherein the natural ligament replacement comprises a bone-tendon-bone graft.

20. The apparatus of claim 18, wherein the natural ligament replacement comprises a semitendinosus.

21. The apparatus of claim 17, wherein the ligament replacement comprises a prosthetic ligament.

22. The apparatus of claim 1, wherein the stop member comprises a ball crimped or welded to the longitudinally extending member.

23. The apparatus of claim 1, wherein the longitudinally extending member comprises a cable or wire.

24. The apparatus of claim 1, wherein the longitudinally extending member comprises a suture.

25. The apparatus of claim 24, wherein the stop member comprises a knot in the suture.

26. The apparatus of claim 1, wherein the longitudinally extending member is removable and disposable.

27. The apparatus of claim 26, wherein the first and second expanding members are conically shaped in part and the conical shape is different on the two members.

28. The apparatus of claim 1, wherein the expanding member and expandable member each comprise a biocompatible plastic.

29. The apparatus of claim 1, wherein the gripping surface of the expandable member comprises serration or grooves.

30. Apparatus for anchoring a ligament or ligament replacement between opposed bones of a bodily joint, comprising:

a first expandable member for insertion into a first borehole formed in a first bone of the joint, the expandable member having an exterior gripping surface for engaging with a sidewall of the first borehole and a central longitudinally extending channel;

the expandable member having a connecting location for connecting to a first end of the ligament or ligament replacement;

a first expanding member for disposition in a proximal end of the channel of the first expandable member for longitudinal movement in the channel to expand the first expandable member in the first borehole; the first expanding member having a longitudinally extending passageway therein aligned with the channel in the first expandable member;

a longitudinally extending member slidably traversing the passageway in the first expanding member and the channel in the first expandable member and extending proximally from the first expanding member for gripping by an installation tool;

a first stop member disposed on the longitudinally extending member for engaging a surface of the first expandable member at a distal end of the channel for preventing further proximal slidable movement of the longitudinally extending member in the passageway and channel;

the first expanding member having a proximal surface for engagement by the installation tool;

the longitudinally extending member being adapted to be grasped by the installation tool with the first stop member abutting the surface of the first expandable member at the distal end of the channel and the installation tool abutting the proximal surface of the first expanding member, the longitudinally extending member being adapted to have a force applied thereto by the installation tool thereby to move the first expanding member relatively with respect to the first expandable member in the channel to expand the first expandable member so that the gripping surface of the first expandable member grips the sidewall of the first borehole to secure the first expandable member in the first borehole and thereby secure the ligament or ligament replacement in the first bone; and further comprising:

a second expandable member for insertion into a second borehole formed in a second bone of the joint opposed to the first bone, the second expandable member having an exterior gripping surface for engaging with a sidewall of the second borehole and a central longitudinally extending channel;

the second expandable member having a connecting location for connecting to a second end of the ligament or ligament replacement;

a second expanding member for disposition in a proximal end of the channel of the second expandable member for longitudinal movement in the channel to expand the second expandable member in the second borehole; the second expanding member having a longitudinally extending passageway therein aligned with the channel in the second expandable member;

the longitudinally extending member slidably traversing the passageway in the second expanding member and the channel in the second expandable member and extending proximally from the second expanding member for gripping by the installation tool;

a second stop member for engaging a surface of the second expandable member at a distal end of the channel for preventing further proximal slidable movement of the longitudinally extending member in the second passageway and second channel;

the second expanding member having a proximal surface for engagement by the installation tool;

the longitudinally extending member being adapted to be grasped by the installation tool with the second stop member abutting the surface of the second expandable member at the distal end of the channel and the installation tool abutting the proximal surface of the second expanding member, the longitudinally extending member being adapted to have a force applied thereto by the installation tool thereby to move the second expanding member relatively with respect to the second expandable member to expand the second expandable member so that the gripping surface of the second expandable member grips the sidewall of the second borehole to secure the second expandable member in the second borehole and thereby secure the ligament or ligament replacement to the second bone.

31. The apparatus of claim 30, wherein the first and second stop members comprise a single stop member, with the longitudinally extending member being movable such that the stop member is movable from a location adjacent the first expandable member to a location adjacent the second expandable member.

32. The apparatus of claim 30, wherein the first and second stop members are different members.

33. A method for anchoring a ligament or ligament replacement into a bone comprising the steps of:

forming a first borehole in the bone;

providing a first expandable member for insertion into the first borehole formed in the bone, the first expandable member having an exterior gripping surface for engaging with a sidewall of the first borehole and a central longitudinally extending channel;

connecting a ligament or ligament replacement to the first expandable member at a connecting location;

providing a first expanding member for disposition in a proximal end of the channel of the first expandable member for longitudinal movement in the channel to expand the first expandable member in the first borehole; the first expanding member having a longitudinally extending passageway therein aligned with the channel in the first expandable member;

disposing a longitudinally extending member slidably traversing the passageway in the expanding member and the channel in the first expandable member and extending proximally from the expanding member for gripping by an installation tool;

providing a stop member on the longitudinally extending member for engaging a surface of the first expandable member at a distal end of the channel for preventing further proximal slidable movement of the longitudinally extending member in the passageway and channel;

the first expanding member having a proximal surface for engagement by the installation tool;

inserting the first expandable member, first expanding member and the longitudinally extending member in the first borehole so that the channel in the expandable member is in alignment with the passageway in the expanding member and the longitudinally extending member traverses the passageway and channel;

grasping the longitudinally extending member with the installation tool with the stop member abutting the surface of the first expandable member at the distal end of the channel and abutting the proximal surface of the first expanding member with the installation tool; and applying a force to the longitudinally extending member with the installation tool thereby to move the first expanding member relatively with respect to the first expandable member to expand the first expandable member so that the gripping surface of the first expandable member grips the sidewall of the borehole to secure the first expandable member in the first borehole and thereby secure the ligament or ligament replacement to the bone.

34. The method of claim 33, further comprising providing a second expandable member and a second expanding member for disposition in a second borehole of an opposed bone of a bone joint for securing a second end of the ligament or ligament replacement to the opposed bone, the longitudinally extending member having a second end traversing through a passageway in the second expanding member and a channel of the second expandable member; and further comprising the steps of:

inserting the second expandable member, second expanding member and the longitudinally extending member in the second borehole so that the channel in the expandable member is in alignment with the passageway in the expanding member and the longitudinally extending member traverses the passageway and channel;

grasping the second end of the longitudinally extending member with an installation tool with a stop member abutting the surface of the second expandable member at the distal end of the channel and abutting the proximal surface of the second expanding member with the installation tool; and applying a force to the second end of the longitudinally extending member with the installation tool thereby to move the second expanding member relatively with respect to the second expandable member to expand the second expandable member so that the gripping surface of the second expandable member grips the sidewall of the second borehole to secure the expandable member in the second borehole and thereby secure the ligament or ligament replacement to the second bone.

35. The method of claim 34, further comprising sliding the longitudinally extending member in the two passageways and channels so that the stop member is movable from a location at a distal end of the channel in the first expandable member to a location at a distal end of the channel in the second expandable member.

36. The method of claim 34, further comprising providing a second stop member on the longitudinally extending member disposed for engagement with a surface adjacent a distal end of the second expandable member.

37. The method of claim 34, further comprising providing the first and second expanding members with different shapes dependent on the hardness of the bone into which the respective expandable member is inserted.

38. The method of claim 34, further comprising applying tension to the ligament or ligament replacement when using the installation tool to fix the second expandable member in the second borehole.

39. The method of claim 33, wherein the ligament or ligament replacement comprises a natural ligament replacement.

40. The method of claim 35, wherein the natural ligament replacement comprises a bone-tendon-bone graft.

41. The method of claim 39, wherein the natural ligament replacement comprises a semitendinosus.

42. The method of claim 33, wherein the ligament replacement comprises a prosthetic ligament.

43. The method of claim 33, further comprising removing the longitudinally extending member once the first and second expandable members have been secured in the respective first and second bones with the ligament or ligament replacement secured therebetween.

44. A surgical fastener for securement into a borehole in an organic medium, comprising:

a first expandable member for insertion into the borehole formed in the organic medium, the expandable member having an exterior gripping surface for engaging with a sidewall of the borehole and a central longitudinally extending channel;

a first expanding member for disposition in a proximal end of the channel of the expandable member for longitudinal movement in the channel to expand the expandable member in the borehole;

the expanding member having a longitudinally extending passageway aligned with the channel in the expandable member;

a longitudinally extending member traversing the passageway in the expanding member and the channel in the expandable member and extending proximally from the expanding member for gripping by an installation tool;

a stop member disposed on the longitudinally extending member for engaging a surface of the expandable member at a distal end of the channel for preventing further proximal slidable movement of the longitudinally extending member in the channel;

the expanding member having a proximal surface for engagement by the installation tool;

the longitudinally extending member being adapted to be grasped by the installation tool with the stop member abutting the surface of the expandable member at the distal end of the channel and the installation tool abutting the proximal surface of the expanding member, the longitudinally extending member being adapted to have a force applied thereto by the installation tool thereby to move the expanding member relatively with respect to the expandable member in the channel to expand the expandable member so that the gripping surface of the expandable member grips the side wall of the borehole to secure the expandable member in the borehole.

45. The surgical fastener of claim 44, wherein the longitudinally extending member comprises a suture and the stop member comprises a knot in the suture.

46. The surgical fastener of claim 45, further wherein the expandable member has a connecting location for connecting to the suture.

47. The surgical fastener of claim 44 wherein the expanding member has grooves or serrations on an exterior surface for engaging with an interior surface of the channel.

48. The surgical fastener of claim 47, wherein the channel has serration or grooves for engaging with the expanding member.

49. The surgical fastener of claim 44, wherein the force comprises an axial force.

50. The surgical fastener of claim 49, wherein the axial force is a pulling force.

51. The surgical fastener of claim 44, wherein the expandable member has a longitudinal slot therein communicating with the channel to assist in expansion.

52. The surgical fastener of claim 51, wherein the expandable member has a plurality of longitudinal slots therein.

53. The surgical fastener of claim 44, wherein the expanding member and expandable member each comprise a biocompatible plastic.

54. The surgical fastener of claim 44, wherein the expanding member is conically shaped.

55. The surgical fastener of claim 44, wherein the gripping surface of the expandable member comprises serration or grooves.

56. The surgical fastener of claim 44, wherein the expanding member has threads on an exterior surface for engaging with threads on an interior surface of the channel.

57. The surgical fastener of claim 56, wherein the expanding member moves rotationally relatively into the expandable member.

* * * * *